United States Patent [19]

Nair et al.

[11] Patent Number: 5,658,794

[45] Date of Patent: Aug. 19, 1997

[54] **METHOD FOR CONTROLLING FUNGAL DISEASE IN TURFGRASSES USING *PSEUDOMONAS AUREOFACIENS* ATCC 55670**

[75] Inventors: Muraleedharan G. Nair, Okemos; Joseph M. Vargas, East Lansing; Jon F. Powell, Lansing, all of Mich.; Amitabh Chandra, Ogden, Utah; Alvin Ronald Detweiler, Haslett, Mich.

[73] Assignee: Board of Trustees operating Michigan State University, East Lansing, Mich.

[21] Appl. No.: 568,781

[22] Filed: Dec. 7, 1995

[51] Int. Cl.$^6$ .............................. C12N 1/12; C12N 1/20
[52] U.S. Cl. .............................. 435/253.3; 435/252.1; 435/822; 435/874
[58] Field of Search .......................... 435/252.1, 253.3, 435/822, 874

[56] References Cited

PUBLICATIONS

Vargas, J. M., Management of turfgrass diseases. Burgess Publishing Co. Minneapolis, MN. 204 (1981).
Burpee, L. L. et al., Phytopathology 74:692–694 (1984).
Goodman, D.M., et al., Phytopathology 81:1438–1446 (1991).
Haygood, R.A., et al., Phytopathology 80:435 (1990).
Nelson, E.G., et al., Plant Disease 75:510–514 (1991).
Melvin, B.P., Biological and cultural management of summer patch and necrotic ring spot.Ph.D. Dissertation (1991).
Thompson, D.C., et al., Phytopathology 82:1123 (1992).
Wong, P.T.W., et al., Annals of Applied Biology 92:191–197 (1979).
Burpee, L. L., et al., Plant Disease 71:97–100 (1987).
Rovira, A.D., et al., The nature and mechanism of suppression.pp. 385–415 in:Biology and Control of Take–All, M.J.C. Asher and J.P. Shipton. eds. Academic Press, New York, NY, 538 pp. (1981).
Cook, R. J., et al., Biological and cultural tests for control of plant diseases. 3:53 (1988).
Smith, A.M., Soil Biology and Biochemistry 8:293–298 (1976).
Glynne, M.D., Annals of Applied Biology 22:225–235 (1935).
Simon, A., et al., Journal of Applied Bacteriology 37:459–460 (1974).
Sarniquet, A., et al., Plant and Soil 145: 11–15 (1992).
Weller, D.M., et al., Phytopathology 73; 463–469 (1983).
Weller, D.M., Annual Review of Plant Pathology 26:379–407 (1988).
Campbell, R., Biological control of microbial plant pathogens Cambridge Univ. Press (1989).
Palleroni, N.J., Pseudomonadaceae. pp. 141–219 in:Bergey's Manual of Systematic Bacteriology, vol. 1, Kreig, N.R. and Holt, J.J., eds. Williams and Wilkins, Baltimore, MD 1024 pp. (1984).
Bull, C.T., et al., Phytopathology 81:954–959 (1991).
Howie, W.J., et al., Phytopathology 77:286–292 (1987).
Kloepper, J.W., et al., Current Microbiology 4:317–320 (1980).
Becker, O., et al., Phytopathology 78:778–784 (1988).
Weller, D. M., et al., Phytopathology 78:1094–1100 (1988).
Alad, Y., et al., Phytopathology 75:1053–1059 (1985).
Shanahan, P., et al., Applied and Environmental Microbiology 58:353–358 (1992).
Vincent, M. N., et al., Applied and Environmental 57:2928–2934 (1991).
Haynes, W. C., et al., J. of Bacteriology 72:412–417 (1956).
Gurusiddaiah, S., et al., Characterization of an antibiotic produced by a strain of *Pseudomonas fluorescens*, etc., Antimicrobial AGents and Chemotherapy 29:488–495 (1986).
Brisbane, P.G., et al., Antimicrobial Agents and Chemotherapy 31:1967–1971 (1987).
Thomashow, L.S., et al., Journal of Bacteriology 170:3499–3508 (1988).
Pierson, L.S., et al., Phytopathology 78:1522 (1988).
Pusey, P.L., et al., Plant Disease 68:753–756 (1984).
Melvin, P. P., et al., Hortscience 28:195–196 (1993).
Bennett, F.T., Annals of Applied Biology 24:236–257 (1937).
Thomashow, L.S., et al., Applied and Environmental Microbiology 56:908–912 (1990).
Baker, C.J., et al., Plant Disease 69:770–772 (1985).
Kohn, L.M., et al., Canadian Journal of Botany 67:371–393 (1989).
Novak, L.A., et al., Applied and Environmental Microbiology 57:525–534 (1991).
Smiley, R. W., Compendium of turfgrass diseases. The American Phytopathological Society, St. Paul, MN. 102 pp. (1992).
Couch, H.B., et al., Phytopathology 50:761–763 (1960).
Smitley, D., et al., Insect, weed and disease management on commercial turfgrass. Michigan State University, East Lansing, MI 28 pp. (1993).
Cole, H., et al., Phytopathology 58:683–686 (1968).
Warren, C.G., et al., Phytopathology 64:1139–1142 (1974).
Vargas, J.M., Jr., et al., Phytopathology 82:1069 (1992).
Detweiler, A.R., et al., Plant Disease 67:627–630 (1983).
Cook, R.N., et al., Plant Disease Reporter 48:254–255 (1964).
Markland, F.E., et al., Agronomy Journal 61:701–705 (1969).
Nelson, E.B., et al., Plant Disease 76:954–958 (1992).
Gilpen et al, "Id. Char. and TN5–Mut. of a Flourescent Pseudomonasal Islol. . . . ", NZ Nat. Sci. 19(0). 1982; pp. 87–94 abstract only.

*Primary Examiner*—John W. Rollins
*Assistant Examiner*—Deborah K. Ware
*Attorney, Agent, or Firm*—Ian C. McLeod

[57] ABSTRACT

A method for controlling fungal diseases in turfgrasses using a *Pseudomonas aureofaciens*. The *Pseudomonas aureofaciens* is particularly useful in inhibiting dollar spot (*Sclerotinia homoeocarpa*) in turfgrasses. The method is environmentally safe and economical.

1 Claim, No Drawings

METHOD FOR CONTROLLING FUNGAL DISEASE IN TURFGRASSES USING *PSEUDOMONAS AUREOFACIENS* ATCC 55670

BACKGROUND OF THE INVENTION

(1) Field of the Invention

The present invention relates to a method for controlling fungal diseases in grasses using a unique strain of *Pseudomonas aureofaciens*. In particular, the present invention relates to novel strains of *Pseudomonas aureofaciens* which inhibit the fungal disease Dollar Spot carried by the fungus (*Sclerotinia homoeocarpa*) which is a major pathogen of turfgrass.

(2) Description of Related Art

Techniques currently employed for the management of fungal turfgrass diseases are highly dependent on the application of chemical fungicides. A broad array of chemical fungicides are currently available for the management of these fungal pathogens. However, the development of resistance to certain classes of chemical fungicides and the failure of agrochemical companies to re-register currently used chemical fungicides with the EPA due to cost and environmental concerns, have promoted research into identification of new chemical fungicides as well as research into alternative disease management strategies. The two major alternatives to the use of chemical fungicides being examined are biological controls and organic or composted fertilizers.

Development of new chemical fungicides generally occurs through the mass screening of novel synthetic compounds. Utilization of antifungal compounds produced by microbial organisms, such as antibiotics, have been highly exploited in the development of medicinal compounds. Application of medicinal antibiotics for the management of plant diseases has been restricted due to concerns of the development of resistance to these compounds by potential human pathogens.

Several bacteria have been identified as producing a variety of classes of compounds that are antifungal in nature, including enzymes, siderophores, hydrogen cyanide, ethylene, and antibiotics. Although all of these compounds have been implicated in biological control activity by bacteria, the commercial application of enzymes for plant disease management is not likely due to their sensitivity to environmental conditions. Another class of compounds that would not be feasible for study are volatile compounds such as hydrogen cyanide and ethylene.

The use of bacteria as biological control agents is one of the fastest growing fields of research in disease management. The concept of the management of disease through the application of soilborne bacteria is attractive due to its sensitivity to environmental concerns. However, significant breakthroughs yielding biological controls that provide consistent disease management have not yet been realized.

*Pseudomonas aureofaciens* is a gram negative rod shaped bacterium, possessing one or more flagella, strictly aerobic, and chemoorganotrophic. *P. aureofaciens* is included in the class of fluorescent pseudomonads and was included taxonomically as a biovar of *Pseudomonas fluorescens* by Stanier et al (Journal of General Microbiology 43:159–271 (1966)). Inclusion of *P. aureofaciens* in the group of fluorescent pseudomonads is based on the ability of most strains to produce fluorescent pigment pyoveridin. The name "*aureofaciens*" literally means to "make golden" which refers to its ability to turn artificial media to a orange-gold color. This color is caused by production of non-fluorescent phenazine pigments. Phenazine pigments reported to be produced by *P. aureofaciens* are phenazine-1-carboxylic acid (PCA), phenazines 2-oxo phenazine and 2-oxo phenazine-1-carboxylic acid (Trutko, S. M., et al., Biokhimima 54:1329–1336 (1990)). Evidence has been presented that the role of phenazine compounds produced by *P. aureofaciens* allows for the removal of excess reducing equivalents from NADH and NADPH under substrate and/or oxygen limitations.

Management of turfgrass diseases has conventionally been conducted through the employment of proper cultural practices and the application of chemical fungicides (Vargas, J. M., Management of turfgrass diseases. Burgess Publishing Co. Minneapolis, Minn. 204 (1981)). One of the more recent instruments of disease management to be examined is the utilization of bacteria and fungi as biological controls. Investigations into the application of biological controls have been conducted toward the management of the turfgrass diseases, brown patch (*Rhizoctonia solani*) (Burpee, L. L., et al., Phytopathology 74:692–694 (1984)), dollar spot (*Sclerotinia homoeocarpa*) (Goodman, D. M., and Burpee, L. L., Phytopathology 81:1438–1446 (1991); Haygood, R. A., et al., Phytopathology 80:435 (1990); and Nelson, E. B., et al., Plant Disease 75:510–514 (1991)), fairy rings (many basidiomycetes) (Smith, J. C., Fairy rings: Biology, antagonism and possible new control methods. Pages 81–85 in: Advances in Turfgrass Pathology. P. O. Larson and B. G. Joyner, eds. Harcourt Brace Jovanovich, Duluth, Minn., 197 pp (1980)), necrotic ring spot (*Leptosphaeria korrae*) (Melvin, B. P., Biological and cultural management of summer patch and necrotic ring spot. Ph.D. Dissertation (1991)), summer patch (*Magnaporthe poae*) (Melvin, B. P., Biological and cultural management of summer patch and necrotic ring spot. Ph.D. Dissertation (1991); and Thompson, D. C., et al., Phytopathology 82:1123 (1992)), take-all (*Gaeumannomyces graminis* (Wong, P. T. W., et al., Annals of Applied Biology 92:191–197 (1979)), and typhula blight (*Typhula incarnata* and *Typhula ishikariensis*) (Burpee, L. L., et al., Plant Disease 71:97–100 (1987)).

The role of microflora in relation to the reduction of disease severity was brought to light with the identification of "suppressive soils". "Suppressive soils" refers to soils which reduce the level of disease intensity to a particular pathogen (Rovira, A. D., et al., The nature and mechanism of suppression. Pages 385–415 in: Biology and Control of Take-All, M. J. C. Asher and P. J. Shipton, eds. Academic Press, New York, N.Y., 538 pp. (1981)). Suppressive soils may be divided into two classes; general antagonism and specific antagonism (Gerlagh, M., Netherlands Journal of Plant Pathology 74:1–97 (1968)).

General antagonism may be found to some degree in all soils and can be directly related to high soil bacteria populations (Rovira, A. D., et al., The nature and mechanism of suppression. Pages 385–415 in: Biology and Control of Take-All, M. J. C. Asher and P. J. Shipton, eds. Academic Press, New York, N.Y., 538 pp. (1981)). Characteristics common to this type of antagonism include the maintenance of soil suppressiveness after heating to 70° C. for 30 minutes, cannot be transferred to other soils, and exhibits greater suppression in undisturbed soils. It is fostered by the addition of organic amendments, increased suppression in soil at temperatures above 25° C., and is promoted by the use of ammonium-nitrogen ($NH_4^+$—N) rather than nitrate-nitrogen ($NO_{3-}$—N) (Cook, R. J., et al., Biological and cultural tests for control of plant diseases. 3:53 (1988)).

Smith (Smith, A. M., Soil Biology and Biochemistry 8:293–298 (1976)) suggested that ethylene ($C_2H_4$) biosynthesis by soil microflora may play a major factor involved in general antagonism. Factors supporting the role of ethylene in general antagonism are that ethylene production in soil increases as soil temperatures increase up to 35° C., is promoted by ammonium-nitrogen but inhibited by nitrate-nitrogen, is fostered by the addition of organic amendments, and is greater in undisturbed bulk soils. Ethylene has also been shown to be inhibitory to G. graminis var. tritici at concentrations less than 5 parts-per-million in the soil atmosphere (Rovira, A. D., et al., The nature and mechanism of suppression. Pages 385–415 in: Biology and Control of Take-All, M. J. C. Asher and P. J. Shipton, eds. Academic Press, New York, N.Y., 538 pp. (1981)).

Specific antagonism occurs through continuous monoculture of a crop in the presence of a pathogen (Gerlagh, M., Netherlands Journal of Plant Pathology 74:1–97 (1968)). This results from the buildup of specific antagonistic microbial populations that are antagonistic to the pathogen. This type of antagonism occurs in soils of lower temperature than general antagonism (15°–25° C.), is eliminated by 60° C. moist heat, can be transferred to other soils by mixing, and is related to the build-up of specific bacteria in the rhizosphere (Cook, R. J., et al., Biological and cultural tests for control of plant diseases. 3:53 (1988)).

One of the most studied models of suppressive soils involves take-all disease of wheat and other grasses as caused by the fungus G. graminis. General antagonism to this disease involves all of the factors previously listed. Research interest has been focused on the phenomenon known as "take-all decline" which is a form of specific antagonism in which "suppression (of take-all) develops with 2 or 3 years of wheat monoculture and severe take-all; the soil becomes "immune" to subsequent outbreaks of take-all if cropped exclusively thereafter to wheat and barley" (Cook, R. J., et al., Biological and cultural tests for control of plant diseases. 3:53 (1988)). This occurrence was first reported by Glynne (Glynne, M. D., Annals of Applied Biology 22:225–235 (1935)) in 1935, who noted a reduction in take-all severity after 4 consecutive wheat crops.

Several studies in the mid 1970's correlated fluorescent pseudomonads with the occurrence of take-all decline. Evaluation of 100 bacterial strains for specific antagonism to G. graminis var. tritici in greenhouse conditions by Cook and Rovira (Cook, R. J., et al., Biological and cultural tests for control of plant diseases. 3:53 (1988)), identified eight (8) strains which yielded suppression greater than or equal to those of natural suppressive soils. All eight strains were Pseudomonas spp., seven of which were fluorescent. Further evaluation of bacterial populations by Cook and Rovira (Cook, R. J., et al., Biological and cultural tests for control of plant diseases. 3:53 (1988)) indicated suppressive soils contained 1000 times more fluorescent pseudomonads than non-suppressive soils. Simon and Ridge (Simon, A., et al., Journal of Applied Bacteriology 37:459–460 (1974)) similarly found 100 to 1000 fold increases of fluorescent pseudomonads on infected root tissues than on healthy roots. Agar plate tests demonstrated that over 70% of the fluorescent pseudomonads isolated from suppressive soils were antagonistic to G. graminis. Increases in fluorescent pseudomonad populations have also been linked with the decline of take-all (*Gaeumannomyces graminis* var. *avenae*) of turfgrass (Sarniguet, A., et al., Plant and Soil 145:11–15 (1992)). Species of fluorescent pseudomonas that are correlated to the development of soil suppressiveness are *P. fluorescens* (Weller, D. M., et al., Phytopathology 73:463–469 (1983)) and *P. aureofaciens* (Cook, R. J., et al., Biological and Cultural tests for control of plant diseases. 3:53 (1988)).

Several mechanisms of pathogen suppression by fluorescent pseudomonads have been proposed. Competition for nutrients and colonization sites has not received recent attention but plays an important role in disease suppression. Bacteria which are capable of using a broad array of nutrients rapidly can reduce carbon and nitrogen sources available for pathogen sporulation and colonization (Weller, D. M., Annual Review of Plant Pathology. 26:379–407 (1988)). Coupled with high metabolism is the ability to undergo rapid reproduction which increases the organisms potential for dispersal and occupation of available niches (Campbell, R., Biological control of microbial plant pathogens Cambridge University Press (1989)). Pseudomonas spp. act in this manner as exemplified by their non-fastidious nature (Palleroni, N.J., Pseudomonadaceae. pages 141–219 in: Bergey's Manual of Systematic Bacteriology, Volume 1, Kreig, N. R. and Holt, J. J., eds. Williams and Wilkins, Baltimore, Md. 1024 pp. (1984)).

The argument for disease suppression by competition emphasizes the importance of colonization in the development of specific antagonistic disease suppression. The degree to which *P. fluorescens* is able to colonize wheat root tissue can be directly correlated with a reduction in the number of root lesions caused by G. graminis var. tritici (Bull, C. T., et al., Phytopathology 81:954–959 (1991)). Colonization of plant roots by bacteria may be divided into two stages (Howie, W. J., et al., Phytopathology 77:286–292 (1987)). Stage I involves the ability of the bacterium to become attached to the plant root. Stage II is dependent on the bacterium's ability to compete for available nutrients. The ability of a bacterium to colonize root tissue is referred to as its competence. Several traits which may play a role in determining a bacterium's rhizosphere competence include surface polysaccharides, presence of flagella and/or fimbriae, chemotaxis, osmotolerance, and the ability to utilize complex carbohydrates (Weller, D. M., Annual Review of Plant Pathology 26:379–407 (1988)).

Siderophores were the first class of metabolic compounds associated with disease suppression by fluorescent pseudomonads (Kloepper, J. W., et al., Current Microbiology 4:317–320 (1980)). Siderophores are "low molecular weight, high affinity iron (III) chelators" (Weller, D. M., Annual Review of Plant Pathology 26:379–407 (1988)). Under conditions of low iron concentrations, these yellow-green fluorescent compounds are excreted by bacteria and complex with available iron. The bacterium is able to recognize and absorb this complex through membrane receptor proteins. It is believed that siderophores sequester iron thereby making it unaccessible to pathogenic fungi. Support for this mode of antagonism has come from studies in which mutants deficient in siderophore production are less suppressive than the siderophore producing parents (Becker, O., et al., Phytopathology 78:778–784 (1988)). Additional evidence has come from studies indicating that the addition of the synthetic iron chelating compound Fe ethylenediamine-di-O-hydroxyphenylacetic acid (Fe EDDA) yields disease suppression. Addition of excess iron in the form of ferric-ethylenediamine-tetraacetic acid (FeEDTA) represses siderophore production and eliminates suppressiveness (Weller, D. M., et al., Phytopathology 78:1094–1100 (1988)). Antibiosis by siderophore activity has been linked to antagonism toward Pythium spp. (Becker, O., et al., Phytopathology 78:778–784 (1988)), *Fusarium oxysporum* (Alad, Y., et al., Phytopathology 75:1053–1059 (1985)), and G. graminis var. tritici (Kloepper, J. W., et al., Current Microbiology 4:317–320 (1980)). Recent work by Hamdan et al., (Hamdan, H., The fluorescent siderophore of Pseudomonas fluorescens: role in suppression of Gaeumannomyces graminis var. tritici and genetic analysis of siderophore production. PhD thesis, Washington State University, Pullman (1988)) involving the generation of siderophore deficient mutants indicate that siderophores have no significant effect on take-all caused by G. graminis var. tritici. Although the role of siderophores in the suppression of G. graminis var. tritici is still in contention, there is little argument regarding it's role in the suppression of Pythium spp. in soil.

Disease suppression of soil pathogens by Pseudomonas spp. has been strongly attributed to the production of antibiotics. Two antibiotics have been attributed to the inhibitory nature of fluorescent pseudomonads, 2,4-diacetylphloroglucinol (DAPG) (Shanahan, P., et al., Applied and Environmental Microbiology 58:353–358 (1992)) and phenazine-1-carboxylic acid (PCA) (Haygood, R. A., et al., Phytopathology 80:435 (1990)). Strain Q2-87 of P. aureofaciens which produces DAPG was identified as being suppressive take-all. DAPG was later confirmed as being a source of antifungal activity of P. aureofaciens Q2-87 on G. graminis var. tritici (Vincent, M. N., et al., Applied and Environmental 57:2928–2934 (1991)).

The production of PCA by P. aureofaciens was first identified by Haynes et al., in 1956 (Haynes, W. C., et al., J. of Bacteriology 72:412–417 (956)). Recent work (Gurusiddaiah, S., et al., Characterization of an antibiotic produced by a strain of Pseudomonas fluorescens inhibitory to Gaeumannomyces graminis var. tritici and Pythium spp. Antimicrobial Agents and Chemotherapy 29:488–495 (1986)) has identified PCA as playing a major role in the inhibitory activity of P. fluorescens against G. graminis var. tritici. Pure crystals of this compound are needle shaped and yellow to green-yellow in color. PCA was shown to be inhibitory to a broad range of fungi with minimum inhibitory concentrations (MIC) to completely prevent fungal growth ranging from 1 to 40 µg/ml on in vitro tests (Gurusiddaiah, S., et al., Characterization of an antibiotic produced by a strain of Pseudomonas fluorescens inhibitory to Gaeumannomyces graminis var. tritici and Pythium spp. Antimicrobial Agents and Chemotherapy 29:488–495 (1986)). Initial reports of the structure of PCA by Gurusiddaiah et al (Gurusiddaiah, S., et al., Characterization of an antibiotic produced by a strain of Pseudomonas fluorescens inhibitory to Gaeumannomyces graminis var. tritici and Pythium spp. Antimicrobial Agents and Chemotherapy 29:488–495 (1986)) proposed that PCA occurred as a dimeric molecule. However, this structure of the antibiotic was later revised by Brisbane et al (Brisbane, P. G., et al., Antimicrobial Agents and Chemotherapy 31:1967–1971 (1987)), who showed that the antibiotic existed in a monomeric state rather than as a dimer.

Thomashow and Weller (Thomashow, L. S., et al., Journal of Bacteriology 170:3499–3508 (1988)) demonstrated the importance of PCA in biological suppression of take-all by P. fluorescens 2–79 through the generation of mutants deficient in PCA production by transposon mutagenesis. All PCA deficient mutants were unable to inhibit G. graminis var. tritici in agar plate tests and provided significantly lower levels of disease suppression in greenhouse studies. Similar studies by Pierson and Thomashow (Pierson, L. S., et al., Phytopathology 78:1522 (1988)) illustrated similar results with P. aureofaciens strain 30–84. Thomashow et al (Thomashow, L. S., et al., Applied and Environmental Microbiology 56:908–912 (1990)) were able to quantify the production of PCA by P. aureofaciens and P. fluorescens on wheat roots grown in steamed and natural soil in the greenhouse. Concentrations of PCA detected in the steamed and natural soils were up to 578 and 133 ng/g root, respectively. PCA was also recovered from the roots of seed treated plants grown in wheat fields (5–12 ng/g root) and in virgin fields (19–27 ng/g root). These results demonstrated the production of antibiotics in the environment and also confirmed that very small amounts of antibiotics delivered to the microsite by biological control agents can be effective in disease management.

The utilization of antibiotics produced by microorganisms such as Penicillium sp (penicillin), Streptomyces griseus (streptomycin), Streptomyces erythraeus (erythromycin), Cephalosporium acremonium (cephalosporin), and several others (Pelczar, M. J., Jr., et al., Microbiology. McGraw-Hill. New York, N.Y. 952 pp. (1977)) for medical uses have been well documented. The potential for application of antibiotics as chemical treatments for plant disease has recently been explored. Application of culture filtrates of Bacillus subtilis provided better management of bean rust than the fungicide mancozeb (Baker, C. J., et al., Plant Disease 69:770–772 (1985)) and protected peaches from infection by Monilinia fructicola (Pusey, P. L., et al., Plant Disease 68:753–756 (1984)). Melvin et al., (Melvin, P. P., et al., Hortscience 28:195–196 (1993)) demonstrated that application of the antibiotic faeriefungin produced by Streptomyces griseus var. autotrophicus provided management of summer patch disease of turfgrass caused by Magnaporthe poae equal to that of the chemical fungicide fenarimol.

Dollar spot is caused by the fungal organism Sclerotinia homoeocarpa F. T. Bennett (Bennett, F. T., Annals of Applied Biology. 24:236–257 (1937)) and is one of the most prevalent diseases of turfgrasses throughout the world (Smiley, R. W., et al., Phytopathology 76:1160–1167 (1985)). It is also the most economically significant disease of turfgrass in the United States and parts of Canada (Goodman, D. M., and Burpee, L. L., Phytopathology 81:1438–1446 (1991); and Vargas, J. M., Management of turfgrass diseases. Burgess Publishing Co. Minneapolis, Minn. 204 (1981)). Inclusion of this organism in the genus of Sclerotinia is currently on a provisional basis. The dollar spot organism produces a flat stroma unlike the sclerotia characteristic of the genus Sclerotinia. Recent work examining the protein composition and anatomy of the stroma (Kohn, L. M., et al., Canadian Journal of Botany. 67:371–393 (1989)) as well as the utilization of electron microscopy and immunological comparisons (Novak, L. A., et al., Applied and Environmental Microbiology 57:525–534 (1991)) suggested that Sclerotinia homoeocarpa should not be included in the genus Sclerotinia. However, proper classification of this organism is not possible as the fertile teliomorph stage of the life cycle is rare or no longer exists. Reexamination of data recorded from fertile teliomorphs collected by Bennett suggested that this organism would be better classified in either the genus Lanzia Sacc. or Moellerodiscus Henn. (Smiley, R. W., Compendium of turfgrass diseases. The American Phytopathological Society, St. Paul, Minn. 102 pp. (1992)).

Turfgrass infected with Sclerotinia homoeocarpa exhibits a bleached or straw-colored appearance. On golf course putting greens and fairways dollar spot lesions appear as sunken spots less than 5 cm in diameter. Under sufficient disease pressure these spots will coalesce and form larger irregular patches. Infected blades initially appear chlorotic and water soaked which become bleached or tan bands traversing the width of the blade with brown margins. Under favorable growth conditions following nights with dew formation, "cobwebs" of white fuzzy mycelium of the fungus may be seen on infected turf (Smiley, R. W., Compendium of turfgrass diseases. The American Phytopathological Society, St. Paul, Minn. 102 pp. (1992); and Vargas, J. M., Management of turfgrass diseases. Burgess Publishing Co. Minneapolis, Minn. 204 (1981)).

High humidity and temperatures ranging from 15° C. to 30° C. are favorable for dollar spot. Dew formation is also conducive to disease development. Much of dew formed is actually guttational water produced by the grass. This guttational water contains carbohydrates and amino acids which may be used as nutrients by the pathogen promoting it to grow and spread. Disease epidemics in Michigan occur in July followed by a second outbreak in late August and early September. The presence of these two separate epidemics may suggest that there may be more than one species of dollar spot, one of which is virulent at temperatures under 20° C., and the other is active at higher temperatures with cool nights (Vargas, J. M., Management of turfgrass diseases. Burgess Publishing Co. Minneapolis, Minn. 204 (1981)). Factors which may increase disease severity include low nitrogen fertility and dry soil conditions (Couch, H. B., et al., Phytopathology 50:761–673 (1960)). Spread of the disease occurs through hyphal growth, and the transport of infected tissue by maintenance equipment and people.

Grasses susceptible to dollar spot in cool weather climates are primarily creeping bentgrass (*Agrostis palustris* Huds.) and annual bluegrass (*Poa annua* L.) although Kentucky bluegrass (*Poa pratensis* L.), perennial ryegrass (*Lolium perenne* L.) and fescues (Festuca spp.) may also be infected. Susceptible grasses in warm weather climates are bermudagrass (*Cynodon dactylon* (L.) Pers.), zoysiagrasses (Zoysia spp.), bahaigrass (*Paspalum notatum* Flugge.), centipedegrass (*Eremochloa ophiuroides* (Munro.) Hack.), and St. Augustinegrass (*Stenotaphrum secondatum* (Walt.) Kuntze) (Vargas, J. M., Management of turfgrass diseases. Burgess Publishing Co. Minneapolis, Minn. 204 (1981)).

Cultural practices may be implemented to reduce disease severity. Maintenance of moderate to high nitrogen fertility will reduce disease intensity and promote plant growth and recovery. Irrigation should be used to maintain adequate soil moisture. Irrigation in the early evening should be avoided in order to decrease the duration of leaf wetness. Removal of guttational water by mechanical means or through irrigation promotes rapid drying of the turf and washes guttational nutrients from the leaf surface. Resistant cultivars of susceptible turfgrass species have not yet been identified or developed. Varieties of turfgrass highly susceptible to dollar spot should not be used.

The use of chemical fungicides as preventative and curative treatment of dollar spot are significant disease management tools. Chemicals currently recommended to manage dollar spot are the contact fungicide chlorothalonil and the systemic fungicides propiconazole, fenarimol, iprodione, triadimefon and vinclozolin (Smitley, D., et al., Insect, weed and disease management on commercial turfgrass. Mich. State University, East Lansing, Mich. 28 pp. (1993)).

Despite the effectiveness of chemical fungicides, *S. homoeocarpa* has developed resistance to several classes of these chemicals. Resistance to fungicides is generally characterized by reduced duration of fungicide effectiveness to a complete failure to manage disease. One of the first studies of resistance to fungicides by *S. homoeocarpa* was conducted by Cole et al (Cole, H., et al., Phytopathology 58:683–686 (1968)). Their findings demonstrated the presence of strains of dollar spot which exhibited reduced levels of sensitivity to the fungicide thiram and identified strains which were 100 times less sensitive to the fungicide cadmium succinate than sensitive strains. Warren et al (Warren, C. G., et al., Phytopathology 64:1139–1142 (1974)) reported the first case of resistance of *S. homoeocarpa* to the benzimidazole class of fungicides (benomyl, thiabendazole, and methyl and ethyl thiophanate). These resistant strains exhibited tolerance to these fungicides over 100 times that of the sensitive strains. Due to the widespread development and persistence of resistance to this class of fungicides, they are no longer recommended for the management of dollar spot (Vargas, J. M., Jr., et al., Phytopathology 82:1069 (1992)). The next systemic fungicides developed to manage dollar spot was iprodione, which belongs to the carboxamide class of fungicides. Detweiler et al (Detweiler, A. R., et al., Plant Disease 67:627–630 (1983)) identified a strain of *S. homoeocarpa* which showed resistance to iprodione at levels 100 times that of the sensitive strains. This iprodione resistant strain also exhibited resistance to the benzimidazole class of fungicides. The most recent class of systemic fungicides released to manage dollar spot are the demethylase inhibitors (DMI) which include the fungicides triadimefon, fenarimol, and propiconazol. Although resistance has been slow to develop, reduced sensitivity has been identified (Vargas, J. M., Jr., et al., Phytopathology 82:1069 (1992)). All fifteen isolates resistant to the DMI fungicides examined have shown resistance to the benzimidazole class of fungicides with two of the isolates showing reduced sensitivity to iprodione. With resistance or reduced sensitivity to all three classes of systemic fungicides used on turf the only effective treatment for these strains remains the use of the contact fungicide chlorothalonil.

One alternative to the chemical fungicides currently being examined is the utilization of organic sources of nitrogen fertilizers for dollar spot disease management. Cook et al (Cook, R. N., et al., Plant Disease Reporter 48:254–255 (1964)) noted differences in the incidence of dollar spot with the use of different nitrogen sources. In these tests an organic form of nitrogen, activated sewage sludge, significantly reduced disease incidence in relation to urea, ammonium sulfate, and ammonium nitrate. The effectiveness of activated sewage sludge in reducing dollar spot incidence was supported by Markland et al (Markland, F. E., et al., Agronomy Journal 61:701–705 (1969)) in a study comparing seven different nitrogen sources. Examination of several compost and organic fertilizers for suppression of dollar spot was conducted by Nelson and Craft (Nelson, E. B., et al., Plant Disease 76:954–958 (1992)). In this study fertilizers were applied as topdressings mixed with 70% sand. Two organic fertilizers (plant and animal meal) tested provided disease management significantly equal to that provided by application of the chemical fungicide propiconazole. Suppression of disease was effective for 30 days after application.

Research into alternative management strategies of dollar spot has also been directed toward the application of biological controls. One of the initial cases of biological control of dollar spot involved application of the fungus *Gliocladium virens*, which has been used in greenhouse conditions to reduce damping off by Pythium spp. and Rhizoctonia spp. (Haygood, R. A., et al., Phytopathology 80:435 (1990)). Bi-weekly applications in the form of alginate prill pellets of *G. virens* spores resulted in reductions of disease severity ranging from 46% to 70% (Haygood, R. A., et al., Phytopathology 80:435 (1990)). Goodman and Burpee (Goodman, D. M., and Burpee, L. L., Phytopathology 81:1438–1446 (1991)), reported significant reductions in disease intensity with top-dressing applications of a sand-cornmeal mixture amended with a fungal strain of *Fusarium heterosporum*, which was isolated from a dollar spot lesion on fine-leaved fescue (Festuca sp.). Significant disease reduction was evident with applications at four week intervals. Topdressing applications at one week intervals resulted in 86% to 98% reductions in disease intensities. The mode of antagonism expressed by this organism is likely to be based on the production of fungi-toxic metabolites. Nelson and Craft (Nelson, E. B., et al., Plant Disease 75:510–514 (1991)), noted significant reductions in dollar spot intensity with topdressing applications of sand-cornmeal amended with strains of the bacterium *Enterobacter cloacae*. As preventative treatments applied at a 30 day interval, the bacterial topdressing provided a 63% reduction in disease severity which was statistically as effective as the fungicide propiconazole. Application of the bacterial amended topdressing on a curative basis was as effective as the fungicide iprodione in reducing disease severity 12 days after application. The mode of dollar spot suppression by *E. cloacae* is not understood, but may be related to the ability of the bacterium to parasitize the fungus through adherence to fungal hyphae (Nelson, E. B., et al., Plant Disease 75:510–514 (1991)).

Objects

It is therefore an object of the present invention to provide novel strains of *Pseudomonas aureofaciens* which inhibit fungi in grasses, particularly Dollar spot. Further, it is an object of the present invention to provide a novel method which uses the novel strains of *P. aureofaciens* to inhibit the fungi. Further still, it is an object of the present invention to provide biological control of the fungi in a manner which is environmentally safe and economical. These and other objects will become increasingly apparent by reference to the following description.

DESCRIPTION OF PREFERRED EMBODIMENTS

The present invention relates to a method for the inhibition of fungal disease of a turfgrass which comprises: repeatedly applying to the turfgrass cultured cells of *Pseudomonas aureofaciens* having the ability to inhibit *Sclerotinia homoeocarpa* on the grass.

Further, the present invention relates to a method for inhibition of fungal diseases of turfgrass which comprises repeatedly applying cultured cells of a *Pseudomonas aureofaciens* selected from the group consisting of one having the identifying characteristics of *Pseudomonas aureofaciens* ATCC 55670 which produces phenazine-1-carboxylic acid based upon fatty acid analysis including mutants thereof which are negative for production of phenazine-1-carboxylic acid.

The strain *Pseudomonas aureofaciens* (Tx-1) is deposited as ATCC 55670 with the American Type Culture Collection, Rockport, Md. The deposit was made on Jul. 31, 1995 under the Budapest Treaty and is available upon request by name and ATCC number. Bacteria strain Tx-1 was isolated at Michigan State University, East Lansing, Mich., from the soil of a turfgrass sample. It was chosen due to the pronounced zone of inhibition surrounding the bacterial colony. The taxonomic disposition of Tx-1 was assessed by fatty acid analysis and by carbon utilization. Reference is also made to Bergey's Manual of Determinative Bacteriology, 9th Edition, for general identification characteristics of *Pseudomonas aureofaciens*.

Fatty acid analysis on Tx-1 was performed by Microcheck, Inc. (Northfield, Vt.) for identification by fatty acid analysis. In this analysis, the fatty acid profile (as determined by gas chromatography of a bacterial whole cell extract) of Tx-1 was compared to the fatty acid profiles of 7000 identified bacterial strains.

Analysis of carbon utilization was conducted using a GN MICROPLATE™ (Biolog, Hayward, Calif.) which provides a standardized method for assaying for a microorganism's ability to utilize 95 different carbon sources. Methods were those included with the GN MICROPLATE™. Inoculated GN MICROPLATES™ were incubated at 28° C. The results of the carbon utilization were recorded as positive (+), negative (−), or indeterminate (/) based on controls provided in the GN MICROPLATE™ and compared to the values of other pseudomonads provided in Bergey's Manual of Determinative Bacteriology. Tx-1 was further compared to fluorescent pseudomonads based on pigmentation.

Results of the fatty acid analysis are provided in the form of a similarity index, in which values from 0.5 to 0.99 suggest an excellent match, while values between 0.1 and 0.3 suggest that the species of the unknown may not be in the database. Similarity indices below 0.1 indicate that the genus of the unknown is questionable. Evaluation of the identity of Tx-1 by fatty acid analysis matched closest to *Pseudomonas aureofaciens*. However, the resulting similarity indices were 0.140, 0.204, and 0.270, suggesting that the species of Tx-1 may not be in the database. Due to concerns of contamination, the test was replicated with a second culture. This resulted with a similarity index of 0.215, which is in agreement with the previous results.

The results of the carbon utilization assay using the GN MICROPLATE™ and the comparison with values provided for relevant pseudomonads are provided in Table 1. Carbon utilization information for relevant Pseudomonas species is listed for ability to utilize given carbon sources. Data listed as differential (d) indicates that the results may be variable within the species. Tx-1 was able to utilize 24 of the 36 carbon sources with one being indeterminate. Comparison of test results with the reported values indicated that the Tx-1 organism differed from *Pseudomonas aeruginosa, Pseudomonas fluorescens, Pseudomonas chlororaphis, P. aureofaciens* and *Pseudomonas putida* by a respective 7, 2, 1, 4 and 5 substrates. This would suggest that the Tx-1 is closest related to *P. fluorescens* or *P. chlororaphis*. However, these results may be swayed by the number of differential results found in *P. fluorescens* and *P. chlororaphis*. It must also be added that it is not uncommon for an individual isolate to lose the ability to utilize a substrate due to a random mutation. If just the cases are considered in which Tx-1 is capable to utilize carbon sources which the defined species are incapable of utilizing (bacteria do not readily pick up metabolic pathways to utilize alternative carbon sources); the Tx-1 isolate differs from *P. aeruginosa, P. fluorescens, P. chlororaphis, P. aureofaciens* and *P. putida* by 6, 0, 1, 1 and 3 carbon sources. This further suggests that Tx-1 would be closest related to *P. fluorescens, P. chlororaphis* and *P. aureofaciens*. Comparison of pigment production between Tx-1 and *P. fluorescens, P. chlororaphis* and *P. aureofaciens* showed that Tx-1 produces an orange non-fluorescent pigment as is characteristic of *P. aureofaciens*. This is compelling support for placing Tx-1 within *P. aureofaciens* as pigment synthesis is a complex trail.

The results of this study suggest that Tx-1 would be best placed within taxon of *P. aureofaciens*. The fatty acid profile of Tx-1 matched closest to that of *P. aureofaciens*. However, the given similarity index was only 0.216 which would indicate that the given species is not in the database. The results of the carbon utilization for Tx-1 did not conclusively identify it as belonging to any of the species within the fluorescent pseudomonads. Carbon utilization patterns of Tx-1 were most similar to those of *P. fluorescens* and *P. chlororaphis*. However, the likelihood of Tx-1 belonging to either of these species is questionable given the fatty acid data, and the fact that neither of these species is identified as producing orange pigmentation. The production of orange pigmentation by Tx-1 further implies that it is related to *P. aureofaciens*. This is further supported by the fact that both *P. aurefaciens* and Tx-1 produce phenazine-1-carboxylic acid, which inhibits the growth of many fungi.

The combined results suggest that Tx-1 is most closely related to *P. aureofaciens*. Compelling support for this comes from the data that the Tx-1 fatty acid profile is most similar to that of *P. aureofaciens*, and that both are known to produce orange pigmentation as well as the antibiotic phenazine-1-carboxylic acid. Based on this information, Tx-1 can be placed within the taxon of *P. aureofaciens*. However, due to the distinct differences in fatty acid profiles, and differences in carbon utilization, it would be most appropriate to identify Tx-1 as a subspecies of the *P. aureofaciens* type strain.

TABLE 2

Pigmentation of Tx-1 and Pseudomonas species.

| Non-fluorescent Pigment | Tx-1 Test | P. fluorescens | P. chloroaphis | P. aureofaciens |
|---|---|---|---|---|
| Green | − | − | + | − |
| Orange | + | − | − | + |
| Blue | − | d | − | − |

The *Pseudomonas aureofaciens* are preferably used in an amount of $2 \times 10^5$ to $2 \times 10^7$ CFU per ml in solution or in a topdressing for the soil. It is preferred to incorporate between about 1 and 10% by weight of a fertilizer for the turfgrass with the *P. aureofaciens*. Most preferably the *P. aureofaciens* is incorporated into the watering system for turfgrass, such as on a golf course.

The strain can be supplied to the golf course or other site as a bacterial concentrate which is frozen or lyophilized. A suitable growth medium or starter medium can be used at the site of use to increase total cell count of the bacteria for application.

EXAMPLE 1

To evaluate Tx-1 as an effective biological control agent, it is important to understand the mode of antagonism of the

TABLE 1

Carbon utilization of Tx-1 and Pseudomonas species

| Substrate | Tx-1 Result | P. aeruginosa | P. fluorescens | P. chlororaphis | P. aureofaciens | P. putida |
|---|---|---|---|---|---|---|
| Acetate | +* | + | + | + | + | + |
| Adonitol | − | − | − | − | − | − |
| Citrate | + | + | + | + | + | + |
| Mannitol | + | + | + | + | + | d |
| Glycerol | + | + | + | + | + | + |
| Erythritol | − | − | d | − | − | − |
| Propionate | + | + | + | + | + | + |
| Putrescine | + | + | + | + | + | + |
| Maltose | / | − | − | − | − | − |
| Sucrose | + | − | + | + | d | − |
| Saccharate | + | − | + | + | + | + |
| β-Hydroxybutyrate | + | + | + | + | + | + |
| Lactate | + | + | + | + | + | + |
| Glucose | + | + | + | + | + | + |
| Trehalose | + | − | + | + | + | + |
| Succinate | + | + | + | + | + | + |
| Sebacate | − | + | − | − | − | − |
| L-Glutamate | + | + | + | + | + | + |
| Sorbitol | − | − | − | − | − | − |
| m-Inositol | + | − | d | + | + | − |
| α-Ketoglutarate | + | + | + | + | + | + |
| Cellobiose | − | − | − | − | − | − |
| L-Alanine | + | + | + | + | + | + |
| L-Proline | + | + | + | + | + | + |
| L-Arabinose | + | − | + | − | + | d |
| L-Rhamnose | − | − | − | − | − | − |
| L-Ornithine | − | + | d | d | + | + |
| L-Phenylalanine | − | d | d | d | + | + |
| L-Threonine | − | − | − | − | − | − |
| L-Serine | − | d | + | d | + | d |
| L-Histidine | + | + | + | + | + | + |
| L-Aspartate | +* | + | + | + | + | + |
| D-Mannose | − | − | − | − | − | d |
| D-Galactose | + | − | + | d | + | − |
| D-Fructose | + | + | + | d | + | + |
| D-Alanine | + | + | + | + | − | + |

*Test results: positive (+), negative (−), indeterminate (/), and differential (d)

bacterial strain. The mode of antagonism by Tx-1 due to the production of antibiotics, can be determined by isolating mutants of this organism which were unable to produce the antibiotic and assaying them against the pathogens.

Materials And Methods

Rifampicin resistant strains of Tx-1 were isolated by first culturing the bacteria in potato dextrose broth (PDB) for 24 hours. Rifampicin medium was prepared by delivering 50 mg of rifampicin in 5 ml of 95% ethanol. This was added to 1 L of autoclaved potato dextrose agar (PDA) cooled to 50° C. Resistant strains were isolated by plating 0.1 ml aliquots of bacterial culture on the rifampicin medium. Resistant strains were removed following 48 hours of growth at 28° C.

Similarity to wild type strains was tested by comparing growth curves. This comparison was initiated by transferring a single colony of each of the test strains and the wild type strains to test tubes of 0.85% saline solution. Serial dilutions were conducted to $10^{-8}$ from which a 0.1 ml aliquot was transferred to test tubes containing 10 ml of PDB. PDB cultures were maintained at 22° C. on a rotary shaker at 100 rpm. Enumeration of colony forming units (CFU) was conducted every 3 hours by performing serial dilutions plated out on PDA medium. This was run for a period of 24 hours.

Bacterial strains that were deficient in the production of antibiotic were isolated from seven day cultures of the rifampicin resistant strain of Tx-1. These cultures were plated on PDA by serial dilution to obtain cell counts of approximately 50 CFUs per plate. Cell colonies that failed to exhibit the characteristic orange pigmentation were isolated and screened against S. homoeocarpa. Plate bioassays were conducted by using a sterile toothpick to transfer a portion of a colony to a PDA plate 0.5 cm from the outer perimeter of the plate. Three sample colonies were assayed per plate along with the parent rifampicin strain which was inhibitory. These plates were cultured for 24 hours at 28° C. A plug of S. homoeocarpa was then transferred to the center of the test plate and incubated for 48 hours at which time the zones of inhibition were evaluated. Stability of non-inhibitory strains was assessed by repeated transfers and bioassays of these new generations of isolates. Two isolates which exhibited growth characteristics most similar to the wild type strains, were compared by following growth curves as described earlier.

Comparison of growth curves of rifampicin resistant strains of Tx-1 with the wild type parents did not show any significant differences except for fatty acid analysis differences. Bacterial strains which did not produce antibiotic were selected on the basis of the lack of orange pigmentation. Antibiosis screening showed no signs of inhibition from the colonies lacking the orange pigmentation which zones of inhibition were evident for the parent strain Tx-1. Other than pigmentation, the antibiotic deficient strains did not exhibit any differences in growth or colony characteristics.

EXAMPLE 2

This Example was conducted to examine the potential of P. aureofaciens strains Tx-1 as a biological control agent of dollar spot Sclerotinia homoeocarpa in the field. To examine the role of the Tx-1 antibiotic in disease antibiosis, the strain of Tx-1 that were isolated and unable to produce the antibiotic in Example 1 were compared to the wild type strains.

Materials and Methods

Biological control studies using P. aureofaciens Tx-1 were conducted at the Hancock Turfgrass Research Center, East Lansing, Mich. A plot of Emerald creeping bentgrass (Agrostis palustris) was used in August of 1992. This stand was naturally infested with S. homoeocarpa many years prior to the start of this research. S. homoeocarpa strains present exhibit resistance to the benzimidazole and dicarboximide classes of fungicides.

The research was carried out with a randomized complete block design with four replications. Plots were 0.9 m×8.1 m (3'×6') with 30 cm (1.5') walkways.

Tx-1 for field application, was fermented by first preparing starter inoculum. A single colony of bacteria was transferred to a test tube containing 10 ml of trypticase soy broth (TSB; Becton Dickinson and Company, Cockeysville, Md.) which was cultured for 24 hours at 22° C. on a rotary shaker at 100 rpm. 1 ml aliquots of these seed cultures were transferred to 2 L erlenmeyer flasks containing 1 L of TSB. Flasks were incubated for 24 hours. Following incubation, 250 ml samples were centrifuged in 250 ml polypropylene flasks using a Sorvall centrifuge. Cells were pelleted at 4000 rpm for 10 minutes. Cell pellets were resuspended in 10 ml TSB. If not used immediately, cell suspensions were stored at 4° C. Following refrigeration, cell suspensions were allowed to adjust to room temperature for 6 to 12 hours prior to application.

Spray application of bacteria were prepared by adding the 10 ml cell suspension to 240 ml of 0.85% by weight saline solution. The total volume was applied to a single plot with the use of a nitrogen gas hand sprayer.

Bacterial topdressing treatments were prepared by amending 58 g of the organic carrier COMPOST PLUS (Ringer Corp., Minneapolis, Minn.) with the 10 ml cell suspensions described previously. COMPOST PLUS is an organic nitrogen source which is a mixture of animal byproducts (bone meal, feather meal, and other organic components) which contain a 7% nitrogen concentration, and was applied at a rate of 32 g/m$^2$ to deliver a rate of 85 g N/100 m$^2$ (¼ lb N/1000 ft$^2$). COMPOST PLUS was applied without the addition of bacteria as a control treatment. A chemical control treatment of the fungicide triadimefon was applied in the form of BAYLETON 25 at a rate of 0.15 g AI/m$^2$.

Treatments were applied on a 14 day schedule. All treatments, except the unfertilized control and COMPOST PLUS treatments, were fertilized with 18-4-10 fertilizer at a rate of 85 g N/100 m$^2$ (½ lb N/1000 ft$^2$) every 14 days.

Data was taken as enumeration of dollar spot patches present within a single plot. Ratings were taken at two week intervals and transformed with the equation:

Data=Log(Number of Spots+1)

Data transformation was conducted to reduce variation at high incidence of disease.

Treatments exhibiting disease reduction from the first years study were replicated the following year. Treatments were applied on a 14 day schedule in Jul. of 1992. COMPOST PLUS was applied to deliver 85 g of N/100 m$^2$ (0.5 lb of N/1000 ft$^2$) and 170 g of N/100 m$^2$ (1.0 lb. of N/1000 ft$^2$) per month. Fertilizer control treatments consisted of the application of 7-3-1 NPK mix, which is similar to the NPK (nitrogen, phosphorus potassium) content of COMPOST PLUS. Fertilizer control treatments were at the same nitrogen levels as COMPOST PLUS. A commercial control agent, triadimefon, was applied at a rate of 0.15 g/m$^2$ every 14 days. Disease ratings were taken weekly and analyzed as previously described.

Only two disease rating dates were included since initial outbreak of dollar spot did not occur until late August 1992 and disease pressure abated in mid September of the same year. Data from the rating dates are included in Table 3. The COMPOST PLUS treatment amended with the antibiotic deficient strain of Tx-1 performed significantly better than the COMPOST PLUS control treatment.

were amended with the maltodextrin to aid in culture stability when applied in the field. Formulated and unformulated cultures were stored at 4° C. until time of application.

TABLE 3

| Treatment | Rate[a] | August 28, 1992 | | September 11, 1992 | |
| --- | --- | --- | --- | --- | --- |
| | | # of Spots | Normalized[b] Data Analysis | # of Spots | Normalized Data Analysis |
| No Treatment | — | 24.3 | 1.40 A[c] | 155.0 | 2.17 A |
| 18-4-10 Fertilizer | 0.85 g N/m$^2$ | 12.7 | 1.11 ABCD | 73.7 | 1.86 A |
| Compost Plus | 32 g/m$^2$ | 5.3 | 0.55 BCDEF | 16.0 | 1.09 B |
| Compost Plus/Tx-1 | 32 g/m$^2$ + 250 ml[d] | 2.0 | 0.43 DEF | 18.3 | 1.28 B |
| Compost Plus/Tx-1$^-$ | 32 g/m$^2$ + 250 ml[d] | 0.3 | 0.10 EF | 5.3 | 0.75 C |
| Compost Plus/Tx-1$^-$ | 32 g/m$^2$ + 250 ml[d] | 2.3 | 0.49 CDEF | 20.3 | 1.21 BC |
| Spray Tx-1 | 250 ml | 11.3 | 0.83 ABCDE | 53.3 | 1.68 AB |
| Spray Tx-1$^-$ | 250 ml | 11.7 | 0.81 ABCDE | 51.3 | 1.68 AB |
| Triadimefon | 0.15 g AI/m$^2$ | 0.0 | 0.00 F | 0.0 | 0.00 D |
| LSD 0.05[e] | | — | 0.69 | — | 0.46 |
| LSD 0.01 | | — | 0.93 | — | 0.63 |
| Std. Deviation | | 3.5 | 0.23 | 11.6 | 0.16 |

[a]Application rates made on plots 0.9 m × 1.2 m.
[b]Data transformation performed as log (# of spots + 1).
[c]Data analyzed with Duncans Multiple Range test, treatments followed by the same letter are not significantly different at the P = 0.05 level.
[d]250 ml of broth concentrated to 10 ml to apply ≈10$^{11}$ CFU/m$^2$ or 10$^6$ CFU/cm$^2$.
[e]Least significant difference values (LSD) are listed for Duncans Multiple Range Test.
Tx-1$^-$ is without antibiotic resistance.
Tx-1 is with antibiotic resistance.

EXAMPLE 3

Two methods of preparing the bacteria were employed. One involved daily culturing of the bacteria 24 hours prior to application. This application procedure assured that the bacteria were metabolically active upon application. The other method involved the culturing of the bacteria prior to the onset of the field season. These bacteria were stored in refrigeration until the time of application. One subset of this group was amended with maltodextrin (10% by weight) in an attempt to improve the stability of the organism upon application.

Materials And Methods

Field evaluation of Tx-1 for the management of dollar spot was conducted at the Hancock Turfgrass Research Center in East Lansing, Mich., on a stand of Pencross creeping bentgrass naturally infested with *S. homoeocarpa*. The study was initiated Jul. 30, 1995 and plots were maintained at 0.5 lb nitrogen/1000 ft$^2$ per month (fertility was not applied during the month of August) with a nitrogen formulation of 18-4-18 N-P-K. Bacterial treatments were applied three times a week using a $CO_2$ hand sprayer. A randomized complete block design was used with four replication and plots which were 0.9 m×1.2 m. Data was recorded on a weekly basis as an enumeration of the number of lesions within a plot.

The bacteria were cultured by two methods. Daily cultures of bacteria were grown in 2 L Trypticase Soy Broth in a 4 L erlenmeyer flask at room temperature, under constant aeration overnight. Bacterial cultures used to examine formulating agents were prepared prior to initiation of the field study. These cultures were grown in A9 media (20 g Brer Rabbit Molasses, 10 g dextrose, and 5 g peptone) in a 10 L Braun fermenter at 26° C. for a period of 72 hours. Following incubation, the bacteria cultures were divided into unformulated and formulated treatments. Formulated treatments were amended with the maltodextrin to aid in culture stability when applied in the field. Formulated and unformulated cultures were stored at 4° C. until time of application.

Quantitation of bacteria for field application was conducted by pelleting cells from 50 ml of broth by centrifugation. The resulting pellet was resuspended in tap water and the optical density was measured using a Spec 20 spectrophotometer at 640 nm. An appropriate amount of culture was applied to deliver $2*10^5$ or $2*10^7$ CFU per cm$^2$.

Control treatments consisting of autoclaved cultures of fresh or refrigerated bacteria to account for possible fertility effects by the bacteria or accompanying media. Autoclaved cultures were applied to deliver the same volumes as bacterial treatments at the $2*10^7$ CFU/cm$^2$ rate. A chemical control was also included which consisted of a spray application of chlorothalonil (Daconil 2787 WDG) at a rate of 3 oz/1000ft$^2$ every 10 days.

Variation in collected data was normalized as the log (number of spots+1). Data was analyzed by Tukeys' Honestly Significant range test using the MSTAT-C statistical software.

Results

Dollar spot disease pressure was not significant until the Sept. 6 rating date and persisted through to early October. Dollar spot ratings are provided in Tables 4 and 5. Application of the precultured bacteria failed to provide significant disease reduction. This may be due to a loss of viability during storage and application or may also be attributed to the bacteria not being metabolically competitive following storage under refrigeration. Only the chemical control chlorothalonil and application of the freshly grown at a rate of $2*10^7$ CFU/cm$^2$ provided a significant reduction in disease incidence with respect to the control. The fresh bacteria at the $2*10^7$ CFU/cm$^2$ rate was also significantly better than the control treatment consisting of autoclaved freshly grown bacteria indicating that disease reduction was not due to fertility effects. This study demonstrated that the bacterial strain Tx-1 was efficacious as a biological control agent for the management of dollar spot when applied frequently at $2*10^7$ CFU/cm$^2$.

Frequent applications can be applied with the BIOJECT system (EcoSoil Systems, Inc. San Diego, Calif.) which couples a bacterial fermentation system to an established irrigation system. One handicap of this Example 3 was that the bacteria were often applied during mid-day during which time the bacteria are most susceptible to UV light. Bacterial applications made through an irrigation system is made at night when the dollar spot fungus is active and there is no UV light. The use of Tx-1 along with higher fertility rates (1 lb N/month) can provide dollar spot management at levels provided by chemical fungicides.

TABLE 4

Dollar spot ratings for September 6 and September 13

| | | September 6, 1995 | | September 13, 1995 | |
|---|---|---|---|---|---|
| Treatment | Rate[a] | Avg. # of Spots | Normalized[b] Data Analysis | Avg. # of Spots | Normalized Data Analysis |
| No Treatment | — | 49.3 | 1.70 A | 30.0 | 1.48 A |
| Fresh Bacteria[c] | $2*10^5$ CFU/cm$^2$ | 37.0 | 1.56 AB | 22.3 | 1.34 AB |
| Fresh Bacteria | $2*10^7$ CFU/cm$^2$ | 27.8 | 1.42 B | 12.5 | 1.01 B |
| Autoclaved Broth[d] | Volume as Above | 40.8 | 1.62 AB | 33.4 | 1.54 A |
| Refrigerated Bacteria[e] | $2*10^5$ CFU/cm$^2$ (Unformulated) | 43.8 | 1.64 AB | 20.5 | 1.32 AB |
| Refrigerated Bacteria | $2*10^7$ CFU/cm$^2$ (Formulated) | 40.5 | 1.61 AB | 22.8 | 1.25 AB |
| Refrigerated Bacteria | $2*10^5$ CFU/cm$^2$ (Unformulated) | 39.0 | 1.59 AB | 24.3 | 1.29 AB |
| Refrigerated Bacteria | $2*10^7$ CFU/cm$^2$ (Formulated) | 45.3 | 1.65 AB | 29.5 | 1.45 AB |
| Sterile Broth[f] | Volume as Above | 34.8 | 1.55 AB | 21.5 | 1.34 AB |
| Chlorothalonil | 0.15 g AI/m$^2$ | 6.3 | 0.85 C | 1.5 | 0.35 C |
| Standard Deviation | | 4.2 | 0.05 | 4.1 | 0.09 |

[a]Application rates made on plots 0.9 m × 1.2 m
[b]Data transformation performed as log (# of spots + 1)
[c]Bacteria cultured on TSB 24 hours prior to application
[d]Bacterial broth autoclaved after 24 hours growth and applied at equal volume to $2*10^7$ CFU/cm$^2$ rate
[e]Bacteria cultured on A9 broth for 72 hours and stored at 4° C. until time of application
[f]Sterile A9 broth applied at equal volume to $2*10^7$ CFU/cm$^2$ (unformulated) rate

TABLE 5

Dollar spot ratings for September 30 and October 4

| | | September 30, 1995 | | October 4, 1995 | |
|---|---|---|---|---|---|
| Treatment | Rate[a] | Avg. # of Spots | Normalized[b] Data Analysis | Avg. # of Spots | Normalized Data Analysis |
| No Treatment | — | 24.3 | 1.40 A | 32.5 | 1.52 A |
| Fresh Bacteria[c] | $2*10^5$ CFU/cm$^2$ | 20.0 | 1.27 AB | 21.8 | 1.31 AB |
| Fresh Bacteria | $2*10^7$ CFU/cm$^2$ | 11.0 | 1.04 B | 13.5 | 1.09 B |
| Autoclaved Broth[d] | Volume as Above | 24.5 | 1.41 A | 34.8 | 1.55 A |
| Refrigerated Bacteria[e] | $2*10^5$ CFU/cm$^2$ (Unformulated) | 20.5 | 1.32 AB | 19.5 | 1.30 AB |
| Refrigerated Bacteria | $2*10^7$ CFU/cm$^2$ (Formulated) | 24.8 | 1.39 A | 27.0 | 1.43 AB |
| Refrigerated Bacteria | $2*10^5$ CFU/cm$^2$ (Unformulated) | 22.8 | 1.36 A | 24.8 | 1.41 AB |
| Refrigerated Bacteria | $2*10^7$ CFU/cm$^2$ (Formulated) | 24.0 | 1.36 A | 28.8 | 1.42 AB |
| Sterile Broth[f] | Volume as Above | 19.8 | 1.30 A | 21.8 | 1.36 AB |
| Chlorothalonil | 0.15 g AI/m$^2$ | 0.3 | 0.08 C | 0.8 | 0.19 C |
| Standard Deviation | | 2.8 | 0.06 | 4.0 | 0.08 |

[a]Application rates made on plots 0.9 m × 1.2 m
[b]Data transformation performed as log (# of spots + 1)
[c]Bacteria cultured on TSB 24 hours prior to application
[d]Bacterial broth autoclaved after 24 hours growth and applied at equal volume to $2*10^7$ CFU/cm$^2$ rate
[e]Bacteria cultured on A9 broth for 72 hours and stored at 4° C. until time of application
[f]Sterile A9 broth applied at equal volume to $2*10^7$ CFU/cm$^2$ (unformulated) rate The foregoing description is only illustrative of the present invention and the present invention is limited only by the hereinafter appended claims.

We claim:
1. A biologically pure culture of *Pseudomonas aureofaciens* ATCC 55670.

* * * * *